(12) United States Patent
Tanaka et al.

(10) Patent No.: US 8,975,203 B2
(45) Date of Patent: Mar. 10, 2015

(54) DIARYLIODONIUM SALT MIXTURE AND PROCESS FOR PRODUCTION THEREOF, AND PROCESS FOR PRODUCTION OF DIARYLIODONIUM COMPOUND

(75) Inventors: Tomoaki Tanaka, Suita (JP); Ikuyo Katsumi, Suita (JP)

(73) Assignee: Nippon Shokubai Co., Ltd., Osaka (JP)

(*) Notice: Subject to any disclaimer, the term of this patent is extended or adjusted under 35 U.S.C. 154(b) by 41 days.

(21) Appl. No.: 13/138,975

(22) PCT Filed: Apr. 30, 2010

(86) PCT No.: PCT/JP2010/057681
§ 371 (c)(1),
(2), (4) Date: Nov. 8, 2011

(87) PCT Pub. No.: WO2010/128649
PCT Pub. Date: Nov. 11, 2010

(65) Prior Publication Data
US 2012/0053048 A1 Mar. 1, 2012

(30) Foreign Application Priority Data

May 8, 2009 (JP) .................................. 2009-113937
May 8, 2009 (JP) .................................. 2009-113938

(51) Int. Cl.
C08F 4/00 (2006.01)
C07C 17/26 (2006.01)
C07C 25/18 (2006.01)

(52) U.S. Cl.
CPC .................. *C07C 25/18* (2013.01); *C07C 17/26* (2013.01)
USPC .......................................... 502/150; 570/206

(58) Field of Classification Search
None
See application file for complete search history.

(56) References Cited

U.S. PATENT DOCUMENTS

| | | | |
|---|---|---|---|
| 3,981,897 A | 9/1976 | Crivello et al. | |
| 4,151,175 A | 4/1979 | Crivello et al. | |
| 4,885,419 A | 12/1989 | Shimizu et al. | |
| 5,340,898 A | 8/1994 | Cavezzan et al. | |
| 5,468,902 A | 11/1995 | Castellanos et al. | |
| 5,550,265 A | 8/1996 | Castellanos et al. | |
| 5,594,042 A | 1/1997 | Glover et al. | |
| 5,624,762 A | 4/1997 | Glover et al. | |
| 5,629,095 A | 5/1997 | Bujanowski et al. | |
| 5,668,192 A | 9/1997 | Castellanos et al. | |
| 5,824,761 A | 10/1998 | Bujanowski et al. | |
| 5,861,467 A | 1/1999 | Bujanowski et al. | |
| 6,084,004 A * | 7/2000 | Weinmann et al. | 522/25 |
| 6,147,184 A | 11/2000 | Castellanos et al. | |
| 6,153,661 A | 11/2000 | Castellanos et al. | |
| 6,232,362 B1 | 5/2001 | Agars et al. | |
| 2001/0041303 A1 | 11/2001 | Sato | |
| 2002/0015826 A1* | 2/2002 | Desmarteau et al. | 428/195 |

FOREIGN PATENT DOCUMENTS

| | | |
|---|---|---|
| DE | 290 651 A5 | 6/1991 |
| JP | 53-101331 | 9/1978 |
| JP | 57-053767 B | 11/1982 |
| JP | 6-41433 | 2/1994 |
| JP | 6-184170 | 7/1994 |
| JP | 7-3028 | 1/1995 |
| JP | 7-055915 B2 | 6/1995 |
| JP | 7-057738 B2 | 6/1995 |
| JP | 7-064764 B2 | 7/1995 |
| JP | 7-116067 B2 | 12/1995 |
| JP | 2001-011185 | 1/2001 |
| JP | 2001-235865 A | 8/2001 |
| JP | 2005-120311 | 5/2005 |
| WO | 99/56177 A1 | 11/1999 |

OTHER PUBLICATIONS

F.Marshall Beringer et al., Journal of American Chemical Society, vol. 81, pp. 342-351 (1959).
Lukasz Kraszkiewicz et al., Synthesis, No. 15, pp. 2373-2380 (2008).
Lukasz Kraszkiewicz et al., Proceeding of ECSOC-9, International Electronic Conference on Synthetic Organic Chemistry, 9th., A022/1-A022/12 (2005).
Extended European Search Report, EP Application No. 10772168.0, Issue Date Jan. 16, 2013.
First Notification of Office Action, CN Patent Application No. 201080019541.9, Issue Date Aug. 20, 2013, Issued by SIPO (The State Intellectual Property Office of P.R. China).
Second Notification of Office Action, CN Patent Application No. 201080019541.9, Issue Date Mar. 31, 2014, Issued by SIPO Examiner.
Notice of Reasons for Refusal, JP Patent Application No. 2010-107645, Issue Date Apr. 22, 2014.
Notice of Reasons for Refusal, JP Patent Application No. 2009-113937, Issue Date Nov. 19, 2013.

* cited by examiner

*Primary Examiner* — Yun Qian
(74) *Attorney, Agent, or Firm* — Masuvalley & Partners (57) ABSTRACT

Disclosed are: a diaryliodonium salt mixture which is a precursor of a $BF_4$ salt or the like of a diaryliodonium compound, can be produced in the form of crystals at ambient temperature, can be purified in a simple manner, can be produced with high efficiency, and can be induced into a $BF_4$ salt or the like salt that has excellent solubility in a monomer or the like; and a process for producing the diaryliodonium salt mixture. Also disclosed is a production process which can achieve good yield and can produce reduced amounts of byproducts, and is therefore applicable to the industrial mass production of a diaryliodonium compound. The diaryliodonium salt mixture is characterized by containing at least two specific diaryliodonium salts.

6 Claims, 4 Drawing Sheets

DIARYLIODONIUM SALT MIXTURE AND PROCESS FOR PRODUCTION THEREOF, AND PROCESS FOR PRODUCTION OF DIARYLIODONIUM COMPOUND

This application is a national phase application under 35 U.S.C. §371 of International Application Serial No. PCT/JP2010/057681, filed on Apr. 30, 2010, and claims the priority benefit under 35 U.S.C. §119 of Japanese Patent Applications No. 2009-113937, filed on May 8, 2009, and No. 2009-113938, filed on May 8, 2009, which are hereby expressly incorporated by reference in their entirety for all purposes.

TECHNICAL FIELD

The present invention relates to a diaryliodonium salt mixture and a method for preparing a diaryliodonium salt mixture, and a method for preparing a diaryliodonium compound.

BACKGROUND OF ART

Salts of diaryliodonium compounds are used as polymerization initiators. For example, in patent documents 1-5, $BF_4$, $PF_6$, $SbF_6$, $AsF_6$ and other salts of diaryliodonium compounds having various side chains have been disclosed as polymerization initiators. These also include bis(dodecylphenyl)iodonium salts.

If the salts of diaryliodonium compounds are used as polymerization initiators, the phenyl moiety may be liberated by decomposition. As a result, for example, such compounds as benzene or toluene may be formed. These compounds have toxicity such as carcinogenicity, and thus their use has been restricted. In contrast to this, applicability of bis(dodecylphenyl)iodonium salts that are substituted with long chain alkyl groups such as dodecyl groups has been anticipated as polymerization initiators since the toxicity of dodecylbenzene produced by decomposition is relatively low.

However, although $BF_4$ salts or the like of diaryliodonium compounds have been employed as polymerization initiators as mentioned above, there have been problems of poor compatibility of bis(dodecylphenyl)iodonium $BF_4$ salts or the like with monomers. Although this problem is not serious at the small laboratory scale preparations of polymers, it may lead to problems of decrease in the efficiency of production at the industrial large-scale production.

Moreover, the $BF_4$ salts or the like of diaryliodonium compounds are usually synthesized from diaryliodonium compounds and salts of halide ions. As halide salts, for example, chloride salts of bis(dodecylphenyl)iodonium have been disclosed in Patent documents 4 and 5. The said chloride salts have been synthesized by the dropwise addition of a mixture of sulfuric acid and acetic acid to dodecylbenzene and potassium iodate in a mixed solvent of acetic acid and acetic anhydride, followed by adding a solution of sodium chloride, cooling it to form a solid, and then recrystallizing the formed solid.

In Non-patent reference 1, examples of preparation of bromide salt and iodide salt of bis(dodecylphenyl)iodonium by a method similar to that of Patent documents 4 and 5 other than finally employing sodium bromide solution or potassium iodide solution have been reported.

Further, the conventional method of preparation of diaryliodonium compounds was not entirely satisfactory, and in particular, efficient method for preparation of diaryliodonium compounds substituted with long chain alkyl groups was not known.

For example, the methods for preparing bis(dodecylphenyl)iodonium salt disclosed in Patent documents 4 and 5 and Non-patent reference 1 deal with reacting potassium iodate ($KIO_3$) and dodecylbenzene in the presence of acetic anhydride and concentrated sulfuric acid. However, this method has a low yield of 37-52%. This cannot be applied to the industrial mass production of diaryliodonium compounds. According to the findings of the present inventors, this method produces large amount of p-iodododecylbenzene as a byproduct. This p-iodododecylbenzene is difficult to separate from the target bis(dodecylphenyl)iodonium salt, and adversely affects the product quality.

Although as examples of preparation of diaryliodonium compounds having smaller substituents such as methyl groups or the like, the Non-patent references 2 and 3 contain example of reaction of sodium periodate ($NaIO_4$) and aryl compounds in presence of concentrated sulfuric acid. Also, examples of preparation of di(4-isobutylphenyl)iodonium salt have been reported in Patent documents 6 through 9.

However, according to the findings of the present inventors, the yields are low when synthesizing diaryliodonium compounds in the absence of acetic anhydride. In other words, since even the yields reported in Non-patent references 2 and 3 are low, the prior art may not be applicable for production of diaryliodonium compounds substituted with long chain alkyl groups. The yields of di(4-isobutylphenyl)iodonium salt having been reported in Patent documents 6 through 9 are also low.

According to the findings of the present inventors, diaryliodonium compounds that are unsubstituted or substituted with lower alkyl groups can be prepared, for example, even by a method employing ammonium persulfate and employing iodobenzene and toluene as raw materials. On the other hand, diaryliodonium compounds substituted with long chain alkyl groups such as dodecyl group, for example, when made from the p-iodododecylbenzene and dodecylbenzene are used as raw materials, never proceed at all under the same conditions. Thus, in the preparation of diaryliodonium compounds, a large difference may be thought to exist in the reactivities of benzene or compounds substituted with lower alkyl groups and compounds having long chain alkyl groups. Therefore, examples of preparation of unsubstituted or lower alkyl substituted diaryliodonium compounds are not necessarily applicable for the preparation of long chain alkyl substituted diaryliodonium compounds.

Moreover, in Patent documents 6 through 9, while $KIO_3$ has been used in the chemical equation, potassium periodate is mentioned in the text instead of potassium iodate. However, since in Patent documents 10 and 11, that refer to Patent documents 6 through 9 as prior art literature relating to the method of preparation of di(4-isobutylphenyl)iodonium salt, it is expressed as potassium iodate, it is thought that potassium iodate may have been wrongly mentioned as potassium periodate in Patent documents 6 through 9. In addition, the use of potassium iodate instead of potassium periodate may be a cause for low yields.

The following is a list of cited documents:
Patent document 1: Japanese Patent Application Publication 2005-120311
Patent document 2: Japanese Patent Application Publication Hei 7-3028 (1995-3028)
Patent document 3: Japanese Patent Application Publication 2001-11185
Patent document 4: Japanese Patent Application Publication Hei 6-184170 (1994-184170)
Patent document 5: Japanese Patent Application Publication Hei 6-41433 (1994-41433)

Patent document 6: Japanese Patent Publication Hei 7-55915 (1995-55915)
Patent document 7: Japanese Patent Publication Hei 7-57738 (1995-57738)
Patent document 8: Japanese Patent Publication Hei 7-64764 (1995-64764)
Patent document 9: Japanese Patent Publication Hei 7-116067 (1995-116067
Patent document 10: Japanese Patent Application Publication 1978-101331
Patent document 11: Japanese Patent Publication 1982-53767
Non-patent reference 1: F. Marshall Beringer and 6 others, Journal of American Chemical Society, vol. 81, pp. 342-351 (1959)
Non-patent reference 2: Lukasz Kraszkiewicz and another person, Synthesis, No. 15, pp 0.2373-2380 (2008)
Non-patent reference 3: Lukasz Kraszkiewicz and another person, Proceedings of ECSOC-9, International Electronic Conference on Synthetic Organic Chemistry, 9th., A022/1-A022/12 (2005)

SUMMARY OF THE INVENTION

Problem to be Solved by the Invention

As mentioned above, conventionally, $BF_4$ salts or the like of diaryliodonium compounds were used as polymerization initiators.

The present inventors have prepared $BF_4$ salts or the like of bis(dodecylphenyl)iodonium as highly safe $BF_4$ salts or the like of diaryliodonium compounds. However, the solubility of these $BF_4$ salts or the like in monomer was poor, and unsuitable for industrial mass production of polymers. Thereupon, to improve the solubility of these $BF_4$ salts or the like in monomers, it was tried to prepare the $BF_4$ salts or the like of a mixture of diaryliodonium compounds substituted with long chain alkyl groups.

However, when the preparation of $BF_4$ salts or the like of a mixture of diaryliodonium compounds substituted with long chain alkyl groups was attempted, since their precursor chloride salts did not crystallize, purification by simple methods such as washing with poor solvents or recrystallization could not be carried out. Accordingly, an industrial mass production is found to be difficult.

As described above, mutually contradictory properties of $BF_4$ salts or the like of diaryliodonium compounds are required, namely, while solubility in monomers is demanded when used as polymerization initiators, it is necessary to obtain as crystals at their precursor for improving the efficiency of manufacture. Further, for using these $BF_4$ salts or the like in such as mass production of polymers, it is necessary to be able to efficiently manufacture the said $BF_4$ salts or the like themselves.

Thereupon, the present first invention intends to provide a mixture of diaryliodonium compounds that, while being the precursors of $BF_4$ salts or the like of diaryliodonium compounds, can be obtained as crystalline materials at ambient temperature, can be easily purified, and can be efficiently prepared, and that also have excellent solubility in monomers when derived to $BF_4$ salts or the like, and to provide a method for the production thereof.

As described above, although there are a few prior arts for manufacturing diaryliodonium compounds substituted with long chain alkyl groups, their number is small and the yields are low. Such low yields prevent the applicability for industrial mass production of diaryliodonium compounds. Moreover, in the said prior art, there is the problem of formation of large amounts of p-iodobenzene compound as the byproduct. Separation of this p-iodobenzene compound from the target diaryliodonium compound is difficult, and the existence of the p-iodobenzene compound adversely affects the product quality.

Thereupon, the present second invention intends to provide a manufacturing method which, due to the fact that the yields are good and the amount of formation of byproduct is also low, may also be suitable for industrial mass production of diaryliodonium compounds.

Means to Solve the Problem

The present inventors carried out extensive studies to solve the problems mentioned above. As a result, the present inventors have discovered that the bromide salts or iodide salts, whose use was avoided because of ease of coloration and low yields, can be obtained as crystals even when the long chain alkyl-substituted diaryliodonium compound was a mixture, and can be efficiently manufactured. Thus, the present first invention was accomplished.

The diaryliodonium salt mixture according to the first present invention is characterized in comprising two or more diaryliodonium salts represented by formula (I):

wherein $R^1$ and $R^2$ are independently $C_{8-20}$ alkyl groups.

The process for production of the diaryliodonium salt mixture according to the first present invention is characterized in that the diaryliodonium salt mixture contains two or more diaryliodonium salts represented by formula (I):

wherein $R^1$ and $R^2$ independently represent $C_{8-20}$ alkyl groups, comprising the steps of:
synthesizing a diaryliodonium mixture containing two or more diaryliodonium compounds represented by formula (III) from an alkylaryl mixture containing two or more alkylaryl compounds represented by formula (II):

wherein $R^3$ is $C_{8-20}$ alkyl group; $R^1$ and $R^2$ are same as described earlier; and adding a bromide salt or a iodide salt of an alkali metal or an alkaline earth metal to a solution of the mixture of diaryliodonium compounds (III).

The present inventors continued extensive studies to solve the problems mentioned above. As a result, the present second invention was accomplished by discovering that the diaryliodonium compounds can be produced in high yield while suppressing the formation of byproduct if the aryl compound is reacted with a periodate in the presence of acetic anhydride and concentrated sulfuric acid.

The process for production of a diaryliodonium compound according to the second present invention is characterized in comprising a step of reacting one or more aryl compounds represented by formula (IV):

(IV)

wherein R is $C_{8-20}$ alkyl group, with a periodate represented by formula $M^1IO_4$ [wherein $M^1$ is an alkali metal] or $M^2(IO_4)_2$ [wherein $M^2$ is an alkaline earth metal] in presence of acetic anhydride and concentrated sulfuric acid;

wherein the target diaryliodonium compound mentioned above is a compound represented by formula (V).

(V)

wherein $R^4$ and $R^5$ are independently same group as R in the said aryl compound (IV).

In the present invention, '$C_{8-20}$ alkyl group' indicates a linear or branched aliphatic hydrocarbon group of 8-20 carbon atoms. If the number of carbon atoms is eight or more, highly toxic lower alkyl benzene does not form by degradation. On the other hand, if the number of carbon atoms exceeds 20, crystallization of the mixture of diaryliodonium salts becomes difficult, and the purification becomes difficult. Therefore, the number of carbon atoms shall be preferably 20 or less. As such groups, for example, n-octyl, n-nonyl, n-decyl, n-undecyl, n-dodecyl, n-tridecyl, n-tetradecyl, n-hexadecyl, n-octadecyl, n-icosyl, methylnonyl, methyldecyl, methylundecyl, methyldodecyl, dimethyloctyl, dimethylnonyl, dimethyldecyl, dimethylundecyl, ethylnonyl, ethyldecyl, ethylundecyl, ethyldodecyl or the like can be exemplified. Among these, $C_{9-18}$ alkyl groups are preferable, and $C_{10-16}$ alkyl groups are more preferable.

EMBODIMENTS OF THE INVENTION

The diaryliodonium salt mixture according to the first present invention is characterized in comprising two or more diaryliodonium salts represented by formula (I):

(I)

wherein $R^1$ and $R^2$ are independently $C_{8-20}$ alkyl groups.

This mixture is crystalline at ambient temperature, and can be easily purified by such simple method as washing. Since it does not become a solid when converted to $BF_4$ salt or the like, it has superior solubility in monomers or the like.

In particular, if the proportion of the most major diaryliodonium salt (I) is 50 mass % or less, then the solubility in monomer or the like when converted to $BF_4$ salt or the like will improve. As the proportion, it is preferably 30 mass % or less, and more preferably 25 mass % or less.

Regarding the number of diaryliodonium salts contained in the mixture of the first invention, it is preferably 3 or more, more preferably 15 or more, furthermore preferably 50 or more, still more preferably 100 or more, and preferably 1000 or less, more preferably 800 or less, furthermore preferably 500 or less, still more preferably 300 or less.

As described above, since the mixture of diaryliodonium salts (I) provided in the first invention, in spite of being crystalline at ambient temperature, do not become solid on derivation to $BF_4$ salt or the like, and have excellent solubility in monomers or the like, it can be employed as a starting material for synthesizing polymerization initiators on an industrially large scale.

The method of production of diaryliodonium provided in the first invention is explained in the order of execution.

In the method according to the first invention, initially, a diaryliodonium mixture containing two or more diaryliodonium compounds (III) is synthesized from an alkylaryl mixture containing two or more alkylaryl compounds (II).

More specifically, for example, a mixture of alkylaryl compounds (II) and iodate or periodate are mixed in acetic anhydride and acetic acid. Dropwise addition of a mixture of concentrated sulfuric acid and acetic acid leads to diaryliodonium sulfates.

Since the alkylaryl compound (II) which is the starting material of the method of first invention has relatively simple structure, they may be purchased if commercially available or may be synthesized from commercially available compounds by known methods to those skilled in the art. For example, by synthesizing benzene having a long chain acyl group as substitutent by Friedel-Crafts reaction of the corresponding acyl chloride and benzene followed by reduction of the carbonyl group, the alkylaryl compound (II) can be easily synthesized.

In the method of the first invention, the mixture of alkylaryl compound (II) is employed as the starting material. This is because diaryliodonium salt which is the target compound should be obtained as a mixture. Though there is no particular limitation on the number of alkylaryl compounds (II) that can be used as the raw material alkylaryl mixture, it is naturally at least 2. To reliably improve the solubility in monomers or the like when the target compound diaryliodonium salt mixture is converted to $BF_4$ salt or the like, the number of alkylaryl compounds (II) shall be preferably 5 or more, and more preferably 10 or more. On the other hand, if the number of alkylaryl compounds (II) is excessively large, there is the risk of the target compound diaryliodonium salt mixture not crystallizing in the purification process. Therefore, the number of alkylaryl compounds (II) is made preferably 50 or less, more preferably 40 or less, still more preferably 30 or less, and furthermore preferably 25 or less.

Although the amounts of each alkylaryl compound (II) contained in the alkylaryl mixture may be suitably adjusted, if the amount of a specific compound is in excess, despite the obtained diaryliodonium salt being a mixture, there is the risk of crystallizing on conversion to $BF_4$ salt or the like. Therefore, the content of the most major alkylaryl compound (II) shall be preferably maintained at 50 mass % or less. If the said alkylaryl mixture is employed as a raw material, apart from obtaining more reliably the diaryliodonium salt mixture as crystal, the said diaryliodonium salt mixture does not become solid at ambient temperature on conversion to $BF_4$ salt or the like, and it will display superior solubility in monomers. As regards such proportion, it is preferably 30 mass % or less, and more preferably 25 mass % or less.

As iodate used in this reaction, there can be mentioned potassium iodate ($KIO_3$) or sodium iodate ($NaIO_3$). In addition, periodates represented by $M^1IO_4$ [in the formula, $M^1$ is an alkali metal] or $M^2(IO_4)_2$ [in the formula, $M^2$ is an alkaline earth metal] can be employed. As alkali metals, there can be mentioned lithium, sodium or potassium. As alkaline earth metals, there can be mentioned magnesium or calcium. Preferably lithium periodate ($LiIO_4$), potassium periodate ($KIO_4$) or sodium periodate ($NaIO_4$) are used.

The use amount of iodate or periodate may theoretically be 0.5 mole times of the alkylaryl mixture. However, they may be used preferably 0.3 mole times or more, more preferably 0.4 mole times or more, and preferably 1 mole times or less, and more preferably 0.8 mole times or less.

Although the proportions of acetic anhydride and acetic acid in the mixture of acetic anhydride and acetic acid into which the alkylaryl mixture and iodate or periodate are added may be suitably adjusted, generally it may be adjusted on the basis of mass ratio to be in the range of acetic anhydride/acetic acid=2/1-1/2.

Even the amount of acetic anhydride and acetic acid mixture can be suitably adjusted, it can be adjusted 1.2 mass times or more, and 3 mass times or less with respect to the amount of the alkylaryl mixture and iodate or periodate used. If the quantity of acetic anhydride and acetic acid mixture is too low, there is the risk of the reaction mixture becoming difficult to agitate, whereas if the amount is too large, purification may become difficult.

In this process, first, the alkylaryl mixture and iodate or periodate are added to the mixture of acetic anhydride and acetic acid, and then mixed. Although this mixed solution may be subjected to reaction as such, it may be cooled in ice since the temperature will increase upon addition of sulfuric acid.

Next, sulfuric acid is added dropwise to the said mixed solution. The sulfuric acid used here is not dilute sulfuric acid, but is called as concentrated sulfuric acid. Sulfuric acid may be used in an amount of 0.5 mole times or more, and 10.0 mole times or less with respect to the aryl compound. If this amount is 0.5 mole times or more, the reaction can progress satisfactorily. On the other hand, if this amount exceeds 10.0 mole times, since it may take time and labor for after-treatment or purification of the reaction liquid, it is preferable to maintain at 10.0 mole times or less. Regarding this quantity, 0.8 mole times or more is especially preferred. If it is 0.8 mole times or more, it becomes possible to obtain the target diaryliodonium compound (V) in high yields with more certainty. More preferably it may be 1 mole times or more and 3 mole times or less. The sulfuric acid that is going to be added dropwise may also diluted with solvents such as acetic acid. In this case, the solvent for dilution can be employed in about 0.2 volume times or more, and 5.0 volume times or less with respect to sulfuric acid.

Since the temperature of the reaction mixture increases when sulfuric acid is added dropwise with the risk of causing the reaction to progress excessively and resulting in the reaction mixture becoming colored, it is preferable to adjust the temperature of the reaction mixture between 30° C. to 60° C. either by adjusting the rate of dropwise addition or by cooling the reaction mixture with water or ice or the like, After the dropwise addition of sulfuric acid, it is preferable to maintain the reaction between the temperature of 10° C. to 100° C. for completing the reaction. Although there is no particular limitation on the reaction time, it can be set between 1 to 10 hours. Specifically, the reaction time can be decided by following the conversion of the alkylaryl compound (II) by $^1$H-NMR or by preliminary experiments or the like.

As treatment after completion of the reaction, conventional methods can be adopted. For example, to remove byproducts and impurities or the like, water may be added and the mixture of the formed diaryliodonium compound (III) may be extracted with an organic solvent.

Since heat is generated when adding water to the reaction mixture, it is better to cool the reaction mixture or to add water dropwise. In addition, the amount of water shall be preferably about 50 volume % to 500 volume % with respect to the reaction mixture. While there is a risk of the byproducts or the like not being adequately removed if the amount of water is too low, on the contrary, there is the risk of decline in productivity if the amount of water is too large.

As organic solvents for extraction of diaryliodonium mixture, there is no particular limitation as long as it has good solubility for this mixture and is immiscible with water, and for example, cyclic hydrocarbon solvents such as cyclohexane, methylcyclohexane, ethylcyclohexane or the like; chain hydrocarbon solvents such as pentane, hexane, heptane, octane, isooctane, isododecane or the like; aromatic hydrocarbon solvents such as benzene, toluene, xylene or the like; and ethers such as diisopropylether, t-butylmethylether, dibutylether or the like, can be used. The obtained extraction solution may also be washed with saturated aqueous sodium hydrogen carbonate solution or aqueous sodium sulfate solution or the like.

$R^1$ and $R^2$, being the substituents of the diaryliodonium compounds (III) contained in the reaction mixture, are same as the substituent $R^3$ of any alkylaryl compound (II) contained in the raw material mixture.

After the completion of the reaction, the diaryliodonium compounds (III) remain dissolved in the said reaction mixture or in the extraction liquid, and exist as iodonium ions. Further, if it is desired to isolate the diaryliodonium compounds (III) in this stage, they are obtained as salts with the anion existing in the said reaction mixture or extraction liquid. As these salts, there can be mentioned sulfate, hydrogen sulfate and acetate.

Next, bromide or iodide of alkali metal or alkaline earth metal is added to the solution of mixture of diaryliodonium compounds (III) to obtain the mixture of compounds (I) which are the diaryliodonium bromide salts or iodide salts.

In this process, the proportion of the diaryliodonium compounds (III) contained in the mixture of diaryliodonium compounds that is present in the largest amount shall be preferably adjusted such that it becomes 50 mass % or less. Similar to the case of starting compounds, according to such an embodiment, apart from obtaining more reliably the diaryliodonium salt mixture as crystal, the said diaryliodonium salt mixture does not become solid at ambient temperature on conversion to $BF_4$ salt or the like, and it will be soluble extremely in monomers. As regards such proportion, it is preferably 30 mass % or less, and more preferably 25 mass % or less.

As alkali metal of the bromide or iodide that can be employed in this reaction, there can be mentioned lithium, sodium and potassium; and as alkaline earth metal, there can be mentioned magnesium and calcium.

Among these bromide and iodide salts, it is preferable to use iodide salts. Regarding the diaryliodonium salt mixture according to the first invention, the iodide salt mixture is obtained in more excellent yields than the bromide salt mixture.

The bromide or iodide of alkali metal or alkaline earth metal may be added as aqueous solution. Although there is no particular restriction on the concentration of the aqueous solution used, it can be about 5 mass % to 80 mass %. Also, there is also no particular restriction on the use quantity of said bromide salt or the like, it may be adjusted so as to be in excess with respect to the mixture of the diaryliodonium compound (III).

After adding the aqueous solution of alkali metal bromide or the like, it may be stirred for about 10 minutes to about 60 minutes, and then separate the liquids. The above operations of stirring after adding aqueous solution and separating the liquids may be repeated two or more times.

Next, the organic phase may be recovered and concentrated under reduced pressure, or a poor solvent may be added to precipitate out the crystals and the crystals may be separated. Prior to that, the organic phase may also be dried with anhydrous magnesium sulfate or the like.

The residue obtained after concentration of the organic phase under reduced pressure mainly contains a plurality of diaryliodonium salts (I) of the first invention, and is crystalline despite being a mixture. Further, as described above, the mixture of diaryliodonium salts (I) provided in the first invention is obtained as crystal even by the addition of a poor solvent to the said organic phase. These crystals may be further purified by such extremely simple methods as washing with poor solvents such as methanol, ethanol, isopropanol or the like and recrystallization.

In the diaryliodonium salt mixture according to the first invention, the proportion of the most major diaryliodonium salt (I) component shall be preferably 50 mass % or less. The said diaryliodonium salt mixture, while excelling in productivity since it is obtained as a crystal, also has the advantage of not becoming solid at ambient temperature when converted to $BF_4$ salt or the like, and having excellent solubility in monomers. Such proportion is preferably 30 mass % or less, and more preferably 25 mass % or less.

Since the mixture of said diaryliodonium salts according to the first invention is crystalline at ambient temperature, it can be purified by industrially applicable simple methods such as washing with a poor solvent and recrystallization. In addition, as it does not become solid at ambient temperature when on conversion to $BF_4$ salt or the like, the solubility in monomers is high, and is thus extremely superior as catalyst used in industrial mass production process. Further, according to the first invention, it is possible to efficiently manufacture a mixture of diaryliodonium salts that is crystalline at ambient temperature, and having high solubility in monomers when converted to such as $BF_4$ salt or the like. Therefore, the first invention is industrially extremely useful as a technology for diaryliodonium salt mixture that are useful as, for example, raw materials for polymerization initiators or the like.

In the method according to the second invention, one or two or more types of aryl compounds (II) is treated with a periodate in presence of acetic anhydride and concentrated sulfuric acid.

Since the alkylaryl compound (IV) which is used in the second invention has relatively simple structure, they may be purchased if commercially available or may be synthesized from commercially available compounds by known methods to those skilled in the art. For example, by synthesizing benzene having a long chain acyl group as substituent by Friedel-Crafts reaction of the corresponding acyl chloride and benzene followed by reduction of the carbonyl group, the alkylaryl compound (IV) can be easily synthesized.

The aryl compound (IV) is a benzene substituted with long chain alkyl group of 8 to 20 carbon atoms, and has lower toxicity towards humans or environment compared to such as toluene substituted with lower alkyl group or unsubstituted benzene or the like. Therefore, even if the diaryliodonium compound (V), which is the target compound of the second invention, decomposes to form the aryl compound (IV) or the aryl compound (IV) substituted with iodine in para-position, it is believed that there will be less harmful effects.

In the method according to the second invention, the aryl compound (IV) may be used alone, or two or more aryl compounds (IV) may be used as raw material. When using two or more aryl compounds (V), it implies that a mixture containing a plurality of diaryliodonium compound (V) is also going to be obtained.

When using two or more types of aryl compounds (IV), as described above, target diaryliodonium compounds (V) will be obtained as a mixture, and although dependent on the type of its counter anion, the crystallizability thereof will decline. For example, when the mixture of aryl compounds (IV) is used as the starting compound as in the example described later, the diaryliodonium compound (V) obtained as the hydrogen sulfate salt, apart from obtaining it as crystal by exchanging its anion with specific material, did not become crystalline when it was separately converted to $BF_4$ salt or the like for use as polymerization initiator. Since such a mixture of diaryliodonium compounds (V), compared to the crystal, has very high solubility in monomers or the like, they are industrially very advantageous.

In the second present invention, a periodate represented by formula $M^1IO_4$ [wherein $M^1$ is an alkali metal] or $M^2(IO_4)_2$ [wherein $M^2$ is an alkaline earth metal] is employed. As alkali metals, there can be mentioned lithium, sodium or potassium. As alkaline earth metals, there can be mentioned, magnesium or calcium. Preferably, lithium periodate ($LiIO_4$), potassium periodate ($KIO_4$) or sodium periodate ($NaIO_4$) are used.

The use amount of periodate may theoretically be 0.5 mole times of the diaryliodonium compound (V). However, they may be used preferably 0.3 mole times or more, more preferably 0.4 mole times or more, and preferably 1 mole times or less, and more preferably 0.8 mole times or less.

Regarding the periodate, only one may be used, or two or more may be mixed and used. Of course, $M^1IO_4$ and $M^2(IO_4)_2$ periodates can be mixed and used.

In the second invention, the reaction is proceeded in presence of acetic anhydride and concentrated sulfuric acid.

Although the reaction mechanism in the second invention is not clear, acetic anhydride and concentrated sulfuric acid are thought to contribute to the formation of reaction intermediate. Moreover, it is also likely that the acetic anhydride is performing the role of eliminating moisture. Regarding the concentrated sulfuric acid referred here, it is a material that practically does not contain water, and it is approximately 95% to 98% sulfuric acid to give an example.

There is no particular restriction on the use quantity of acetic anhydride, and it may be determined by preliminary experiments or the like. Usually, it is about 0.5 mole times to 10.0 mole times with respect to the aryl compound (IV). If this amount is 0.5 mole times or more, the reaction can progress more satisfactorily. On the other hand, since if this amount exceeds 10.0 mole times, it may take time and labor for after-treatment or purification of the reaction liquid, it is preferable to maintain at 10.0 mole times or less. Regarding this quantity, 0.8 mole times or more is more preferable. If it is 0.8 mole times or more, it becomes possible to obtain the target diaryliodonium compound (V) in high yields with more certainty.

There is also no particular limitation on the use amount of concentrated sulfuric acid. Usually, it is 0.4 mole times to 10.0 mole times with respect to the aryl compound (IV). If this amount is 0.4 mole times or more, the reaction can progress more satisfactorily. On the other hand, since if this amount exceeds 10.0 mole times, it may take time and labor for after treatment or purification of the reaction liquid, it is preferable to maintain at 10.0 mole times or less. Regarding this quantity, 0.8 mole times or more is more preferable. If it is 0.8 mole times or more, it becomes possible to obtain the target diaryliodonium compound (V) in high yields with more certainty.

In the method according to the second invention, solvents may also be used. There is no particular limitation on the type of the solvent, and may be appropriately selected. As the solvent, carboxylic acids such as acetic acid, formic acid, propionic acid, butyric acid, valeric acid, and caproic acid or the like can be exemplified.

In the method according to the second invention, concentrated sulfuric acid may be added to the mixture of the aryl compound (IV), periodate and acetic anhydride, or the aryl compound (IV) and concentrated sulfuric acid may be added dropwise to a mixture of periodate and acetic anhydride. Furthermore, periodate may also be added in several lots. This mixture may be diluted to about 1.2 volume times to 10.0 volume times by adding solvent. Similar to the case above, concentrated sulfuric acid may also be diluted to 1.5 volume times to 10.0 volume times by adding solvent. Of course, it is also possible to dilute only either of them.

If concentrated sulfuric acid is added to the above mixture, heat will be generated. Therefore, by adjusting the speed of addition through dropwise addition of concentrated sulfuric acid, or through cooling during adding or the like, the reaction mixture temperature during addition is maintained preferably between about 10° C. and 70° C.

After the completion of addition of concentrated sulfuric acid, the reaction is continued further. Regarding the reaction temperature during this, about 10° C. to 100° C. is preferable. At 10° C. or higher, the reaction can progress more satisfactorily. More preferably, the reaction is carried out at about 50° C. to 60° C. If the reaction temperature is 50° C. or more, the reaction progresses extremely well, and the target diaryliodonium compound (V) is obtained in high yield.

Regarding the reaction time after the addition of concentrated sulfuric acid, although it may be suitably adjusted, it is usually about 1 to 10 hours. Moreover, it is preferable to perform the preparation of the above mixed solution, addition of concentrated sulfuric acid, and subsequent reaction under the flow of inert gas such as nitrogen or argon or the like.

As after-treatment after completion of the reaction, conventional methods can be adopted. For example, although the target diaryliodonium compound (V) exists in the reaction mixture as hydrogen sulfate salt, as its lipophilicity is high, it can be extracted with a lipophilic organic solvent. On the other hand, it is necessary to remove sulfuric acid or the like. Therefore, it is preferable to separate the liquids by adding lipophilic organic solvent and water, and extract the diaryliodonium compound (V).

As lipophilic organic solvents, there is no particular limitation as long as it can extract the diaryliodonium mixture and is immiscible with water, and for example, cyclic hydrocarbon solvents such as cyclohexane, methylcyclohexane, ethylcyclohexane or the like; chain hydrocarbon solvents such as pentane, hexane, heptane, octane, isooctane, isododecane or the like; aromatic hydrocarbon solvents such as benzene, toluene, xylene or the like; and ethers such as diisopropyl ether, t-butyl methyl ether, dibutyl ether or the like can be used.

As heat will be generated during the addition of water to reaction mixture, it is preferable to cool the reaction mixture.

The obtained organic phase may be washed with water, aqueous sodium hydrogen carbonate solution, aqueous sodium hydrogen sulfate solution, aqueous sodium carbonate solution and aqueous sodium sulfate solution or the like. Moreover, drying may also be done with anhydrous sodium sulfate or anhydrous magnesium sulfate or the like.

Next, the target diaryliodonium compound (V) from the organic phase may be purified by crystallization or the like. During crystallization, if the byproduct p-iodo alkylbenzene is present in large amounts, its complete removal is extremely difficult. However, since the formation of the byproduct has been suppressed in the method of the second invention, the crystallizability of the obtained diaryliodonium compound is excellent, and a high purity diaryliodonium compound (V) can be obtained. Further, although it takes for solid-liquid separation after crystallization if the byproducts are more in quantity, the solid-liquid separation can also be executed faster according to the method of the second invention.

According to the second invention, diaryliodonium compounds, which can be used as precursors for polymerization initiators or the like and are safer, can be manufactured in high yield and easily, while suppressing the formation of byproducts. Therefore, the second invention is industrially extremely useful for the commercial mass production of diaryliodonium compounds.

EXAMPLES

Below, the present invention is further concretely explained by offering examples, however, the present invention is not limited by the following examples, and it is also possible to practice by suitably modifying within the scope appropriate for the purposes mentioned earlier and later, and all those will be included within the technical scope of the present invention.

Examples and comparison examples of the first invention will be described hereinbelow.

Example 1

Production of Diaryliodonium Bromide Salt Mixture

Alkene L (product of Nippon Oil Corporation, mean molecular weight: 241), which is a mixture of benzenes substituted with $C_{10-13}$ long chain alkyl, was analyzed by GC-MS and molecular weight corresponding to each peak was determined. From the area ratio of each peak, the content of each component was calculated. Results are shown in Table 1.

TABLE 1

| No. | Peak (min) | Molecular formula | Molecular weight | Peak area ratio |
|---|---|---|---|---|
| 1 | 8.31 | Ph—$C_{10}H_{21}$ | 218 | 3.4 |
| 2 | 8.41 | | | 2.6 |
| 3 | 8.63 | | | 2.5 |
| 4 | 9.06 | | | 2.5 |
| 5 | 9.45 | Ph—$C_{11}H_{23}$ | 232 | 13.0 |
| 6 | 9.59 | | | 6.3 |
| 7 | 9.88 | | | 6.5 |
| 8 | 10.38 | | | 5.8 |
| 9 | 10.73 | Ph—$C_{12}H_{23}$ | 246 | 8.5 |
| 10 | 10.80 | | | 8.0 |
| 11 | 10.99 | | | 6.0 |
| 12 | 11.36 | | | 6.1 |
| 13 | 12.02 | | | 5.4 |
| 14 | 12.37 | Ph—$C_{13}H_{27}$ | 260 | 8.0 |
| 15 | 12.50 | | | 5.0 |
| 16 | 12.76 | | | 3.7 |
| 17 | 13.27 | | | 3.4 |
| 18 | 14.15 | | | 3.2 |

According to the above results, Alkene L contains 18 types of long chain alkyl benzenes, and the content of each was 13.0% at the highest.

Figure 1:
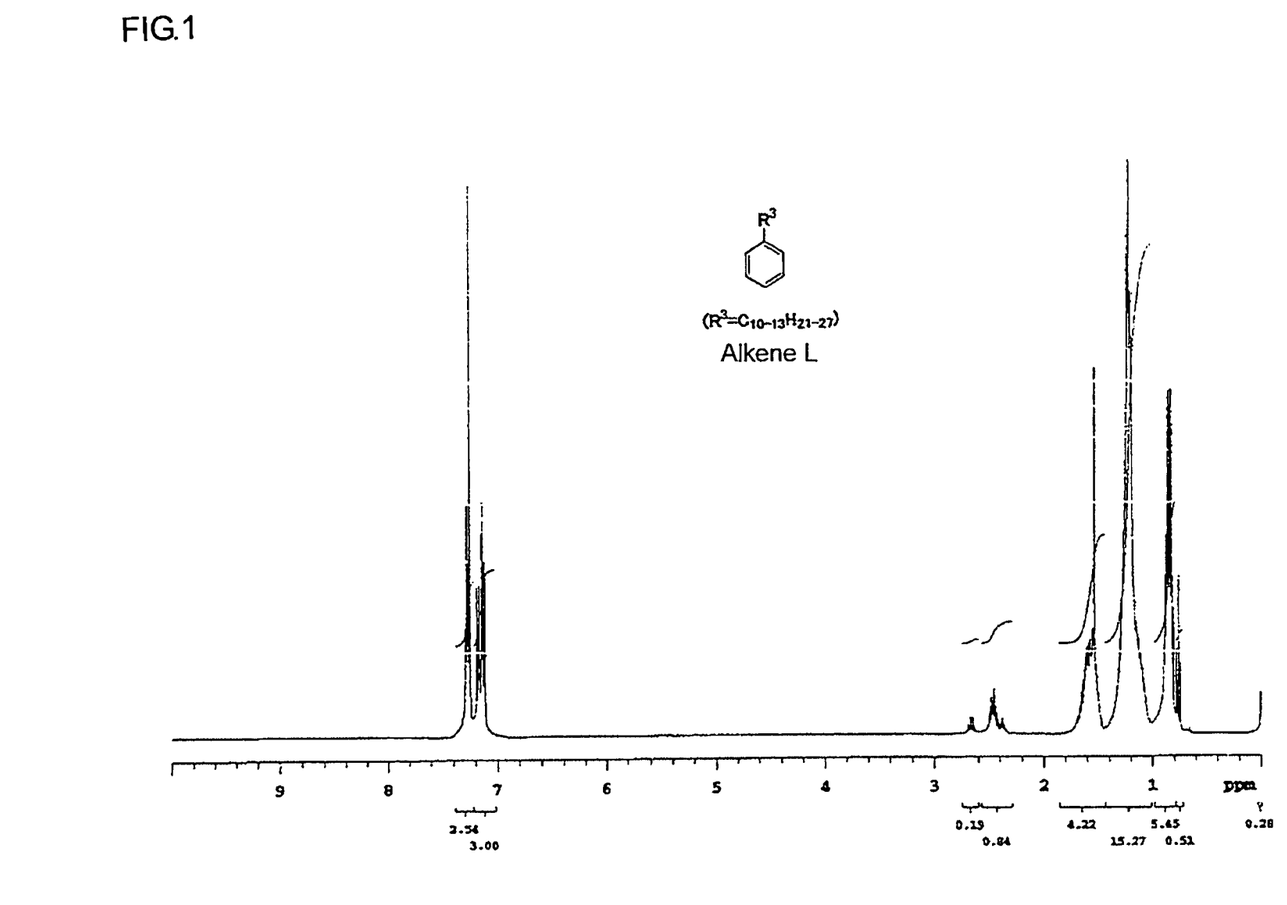
FIG. 1 is the $^1$H-NMR chart of the mixture of alkylaryl compounds employed as raw material in the method of the first invention.
Figure 2:
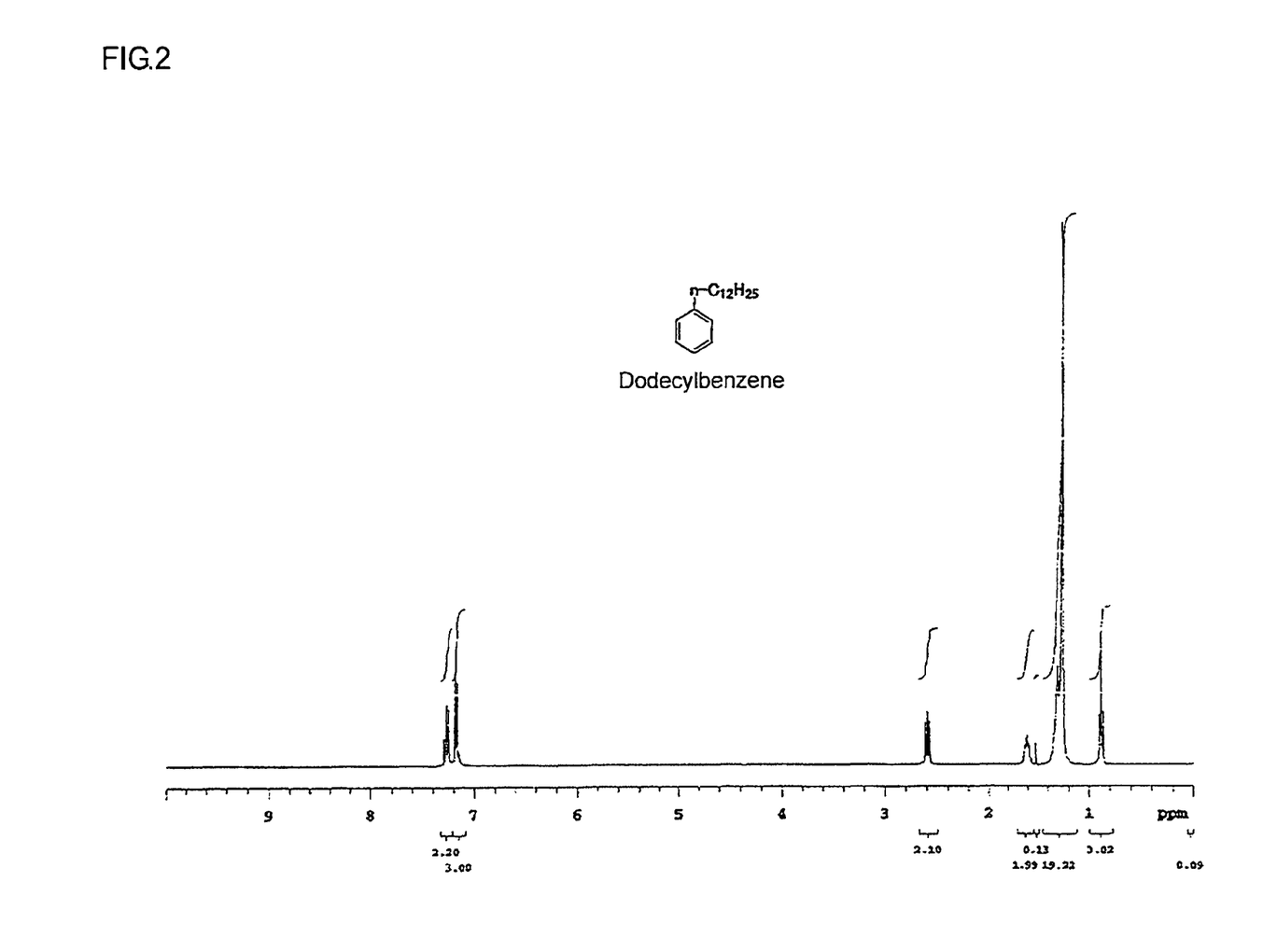
FIG. 2 is the $^1$H-NMR chart of dodecylbenzene.

The $^1$H-NMR chart of Alkene L is shown in FIG. 1. As per FIG. 1, near 2.3-2.7 ppm, 3 broad peaks due to protons of methylene (—$CH_2$— group) or methine group (—CH< group) directly linked to benzene ring can be found. Further, near 0.7-1.8 ppm, there are complex peaks due to protons in alkyl groups other than those mentioned above. For sake of comparison, the $^1$H-NMR chart of dodecylbenzene is shown in FIG. 2. As per FIG. 2, near 2.3-2.7 ppm, there is only a triplet due to the (—$CH_2$— group) directly linked to the benzene ring. Further, the peak near 0.8-1.6 ppm is very simple compared to FIG. 1. As above, even from $^1$H-NMR chart, it is found that Alkene L is a mixture of benzenes substituted with a variety of alkyl groups.

Figure 3:
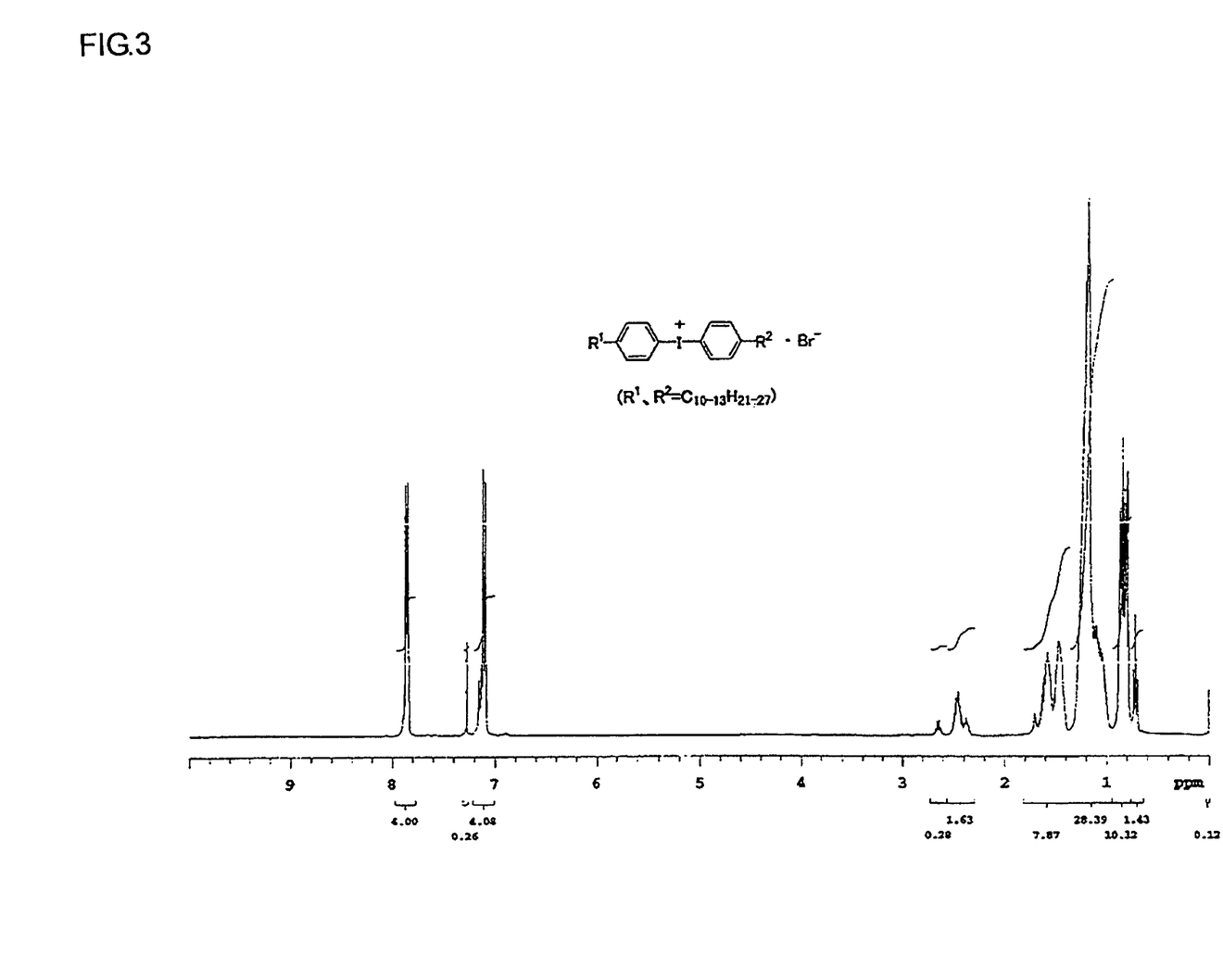
FIG. 3 is $^1$H-NMR chart of diaryliodonium bromide salt mixture according to the first invention.

Into a 4-neck flask equipped with a reflux condenser, dropping funnel, nitrogen inlet tube and thermometer were charged Alkene L (product of Nippon Oil Corporation, 50.00 g), potassium iodate (21.44 g), acetic anhydride (51.00 g) and acetic acid (99.04 g) were added, and the atmosphere inside the reaction vessel was purged with nitrogen. A mixture of concentrated sulfuric acid (29.46 g) and acetic acid (20.20 g) was taken inside the dropping funnel, and while flowing nitrogen gas, was added dropwise during 1.5 hours such that the reaction temperature did not exceed 40° C. After the completion of addition, the reaction mixture was stirred for 2 hours at 40° C. Then, while cooling, water (100.44 g) was added dropwise to the reaction mixture. Further, hexane (100.68 g) was added to the reaction mixture and stirred for 30 minutes. From the reaction mixture that had separated into two layers, the organic phase was recovered, and washed with saturated aqueous sodium hydrogen carbonate solution (200.80 g). Separately, potassium bromide (12.80 g) was dissolved in water (101.19 g) and the obtained aqueous potassium bromide solution was added to the organic phase (200.08 g), stirred for 30 minutes, and from the reaction mixture that had separated into two layers, the organic phase was recovered. Separately, potassium bromide (5.30 g) was dissolved in water (101.89 g), and after washing the organic phase with the obtained aqueous potassium bromide solution, the organic phase was concentrated under reduced pressure. The obtained residue was in solid. Isopropanol (252.87 g) was added to this residue, stirred, and the solid material was filtered. Washing the obtained solid substance with isopropanol, and drying under reduced pressure at 60° C. gave diaryliodonium bromide salt mixture (weight: 15.50 g, yield: 22.5%). When the obtained bromide salt was analyzed by $^1$H-NMR, as in FIG. 3, complex peaks due to multiple side chain alkyl groups were seen, and thus confirmed to be a mixture, peaks due to raw material or byproducts were almost absent, and thus its purity was very high.

Example 2

Production of Diaryliodonium Iodide Salt Mixture

Figure 4:
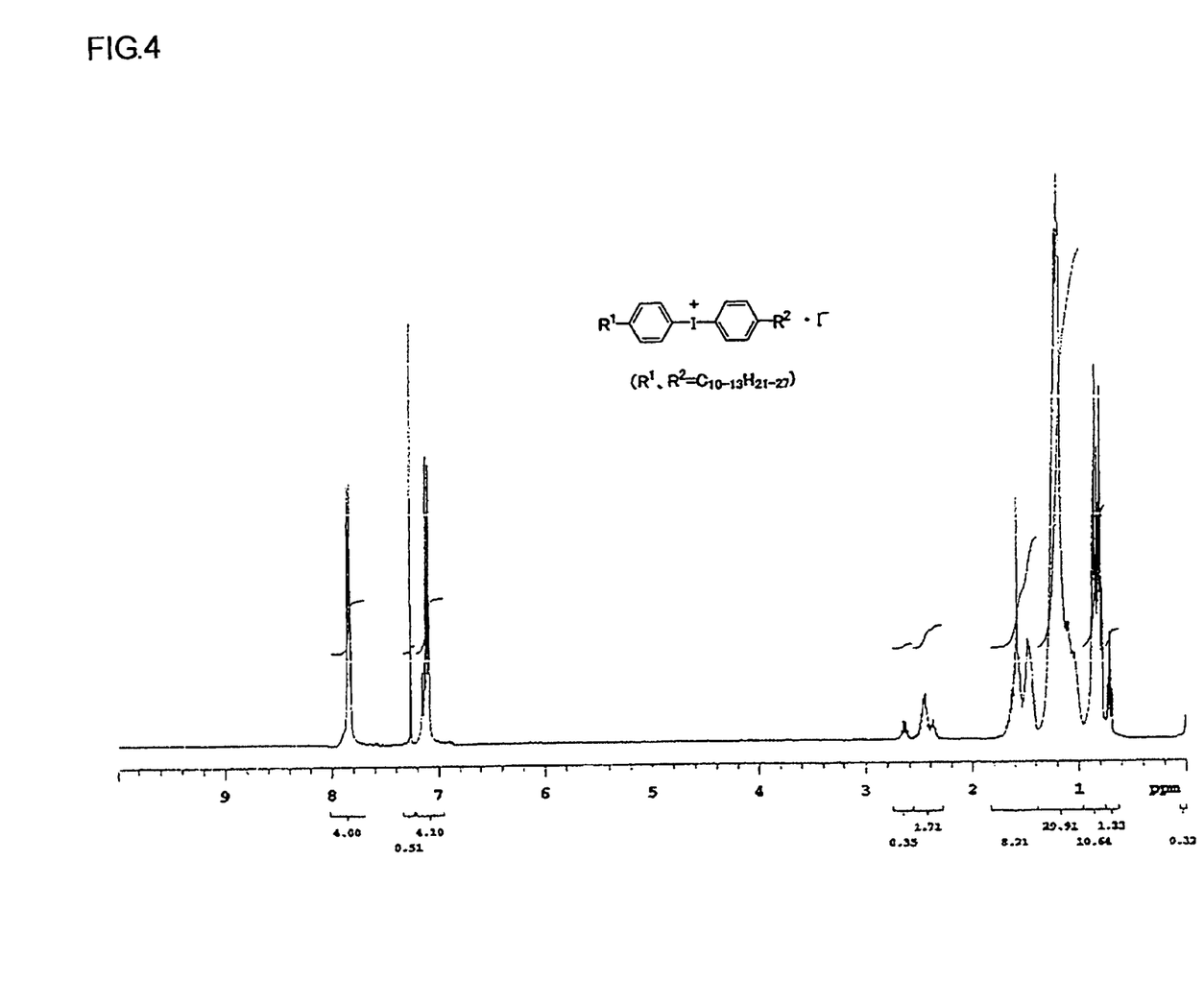
FIG. 4 is $^1$H-NMR chart of diaryliodonium iodide salt mixture according to the first invention.

Into a 4-neck flask equipped with a reflux condenser, dropping funnel, nitrogen inlet tube and thermometer were charged Alkene L (product of Nippon Oil Corporation, 150.06 g), potassium iodate (66.56 g), acetic anhydride (158.90 g) and acetic acid (150.26 g) were added, and the atmosphere inside the reaction vessel was purged with nitrogen. A mixture of concentrated sulfuric acid (91.66 g) and acetic acid (60.16 g) was charged into the dropping funnel, and while flowing nitrogen gas, added dropwise over 1 hour such that the temperature of the reaction mixture did not exceed 40° C. After the completion of addition, the reaction mixture was stirred for 2 hours at 40° C. Then, while cooling, water (300.82 g) was added dropwise to the reaction mixture. Further, cyclohexane (150.42 g) was added to the reaction mixture and stirred for 30 minutes. From the reaction mixture that had separated into two layers, the organic phase (436.66 g) was obtained. Separately, a sodium iodide solution obtained by dissolving sodium iodide (156.00 g) in water (56.48 g) was added to the organic phase, and stirred for 30 minutes. The reaction mixture was separated into layers, and the organic phase (460.00 g) was obtained. On addition of methanol (778.00 g) and ethanol (778.76 g) to this organic phase, a precipitate was formed. The obtained precipitate was filtered, and after washing with ethanol (240.00 g), and drying under reduced pressure at 60° C., diaryliodonium iodide salt mixture was obtained (weight: 114.64 g, yield: 50.2%). As per these results, regarding the diaryliodonium salt mixture of the present invention, it is possible to obtain the iodide salt mixture in higher yield. When the obtained iodide salt was analyzed by $^1$H-NMR, as in FIG. 4, complex peaks due to multiple side chain alkyl groups were seen, and thus confirmed to be a mixture, peaks due to raw material or byproducts were almost absent, and thus its purity was very high.

Example 3

Production of Diaryliodonium Iodide Salt Mixture

Dodecylbenzene soft type (product of Tokyo Kasei Co., Ltd., mean molecular weight: 246.43 g), which is a mixture of benzenes substituted with long chain alkyl groups of 10 to 13 carbon atoms, was analyzed by GC-MS, and the molecular weight corresponding to each peak was determined. From the area ratio of each peak, the content of each component was calculated. Results are shown in Table 2.

TABLE 2

| No. | Peak (min) | Molecular formula | Molecular weight | Peak area ratio |
|---|---|---|---|---|
| 1 | 8.31 | Ph—$C_{10}H_{21}$ | 218 | 2.3 |
| 2 | 8.41 | | | 1.8 |
| 3 | 8.63 | | | 1.8 |
| 4 | 9.06 | | | 2.0 |
| 5 | 9.45 | Ph—$C_{11}H_{23}$ | 232 | 15.2 |
| 6 | 9.59 | | | 7.6 |
| 7 | 9.88 | | | 6.9 |
| 8 | 10.38 | | | 7.0 |
| 9 | 10.73 | Ph—$C_{12}H_{25}$ | 246 | 9.2 |
| 10 | 10.80 | | | 8.5 |
| 11 | 10.99 | | | 6.5 |
| 12 | 11.36 | | | 6.0 |
| 13 | 12.02 | | | 5.8 |
| 14 | 12.37 | Ph—$C_{13}H_{27}$ | 260 | 6.7 |
| 15 | 12.50 | | | 4.2 |
| 16 | 12.76 | | | 3.2 |
| 17 | 13.27 | | | 2.8 |
| 18 | 14.15 | | | 2.6 |

According to the above results, Dodecylbenzene soft type contains 18 types of long chain alkyl benzenes, and the content of each was 15.2% at the highest.

Into a 4-neck flask equipped with a reflux condenser, dropping funnel, nitrogen inlet tube and thermometer were charged Dodecylbenzene soft type (product of Tokyo Kasei Co., Ltd., 108.94 g), potassium iodate (47.01 g), acetic anhydride (113.66 g) and acetic acid (221.10 g) were added, and the atmosphere inside the reaction vessel was purged with nitrogen. A mixture of concentrated sulfuric acid (65.21 g) and acetic acid (44.14 g) was charged into the dropping funnel, and while flowing nitrogen, added dropwise over 1 hour such that the temperature of the reaction mixture did not exceed 40° C. After the completion of addition, the reaction mixture was stirred for 2 hours at 40° C. Then, while cooling, water (201.46 g) was added dropwise to the reaction mixture. Further, ethylcyclohexane (100.00 g) was added to the reaction mixture and stirred for 30 minutes. From the reaction mixture that had separated into two layers, an organic phase (294.02 g) was obtained. Separately, a sodium iodide solution obtained by dissolving sodium iodide (166.35 g) in water (109.28 g) was added to the organic phase, and stirred for 30 minutes. The reaction mixture separated into layers, and an organic phase was obtained. On addition of methanol (546.84 g) and ethanol (547.71 g) to this organic phase, a precipitate was formed. The obtained precipitate was filtered, and after washing with methanol (150.91 g), and drying under reduced pressure at 60° C., diaryliodonium iodide salt mixture was obtained (weight: 704.25 g, yield: 42.9%).

Comparison Example 1

Production of Diaryliodonium Chloride Salt Mixture

Into a 4-neck flask equipped with a reflux condenser, dropping funnel, nitrogen inlet tube and thermometer were charged Alkene L (product of Nippon Oil Corporation, 20.02 g), potassium iodate (8.88 g), acetic anhydride (12.084 g) and acetic acid (39.972 g) were added, and the atmosphere inside the reaction vessel was purged with nitrogen. A mixture of concentrated sulfuric acid (12.00 g) and acetic acid (8.138 g) was charged into the dropping funnel, and while flowing nitrogen, added dropwise over 1 hour such that the temperature of the reaction mixture did not exceed 40° C. After the completion of addition, the reaction mixture was stirred for 2.5 hours at 40° C. Then, while cooling, water (50.10 g) was added dropwise to the reaction mixture. Further, cyclohexane (504.06 g) was added to the reaction mixture and stirred for 30 minutes. From the reaction mixture that had separated into two layers, an organic phase (294.02 g) was obtained. Separately, a sodium chloride solution obtained by dissolving sodium chloride (2.91 g) in water (9.03 g) was added to the organic phase, and stirred for 30 minutes. The reaction mixture separated into layers, and an organic phase was obtained. Separately, a sodium chloride solution obtained by dissolving sodium chloride (2.81 g) in water (8.69 g) and after washing the organic phase with the obtained aqueous sodium chloride solution, the organic phase was concentrated under reduced pressure.

However, since the obtained residue did not solidify, it could not be purified by simple method such as washing with poor solvent.

Examples and comparison examples of the second invention will be described hereinbelow.

Example 4

Production of Diaryliodonium Compound Using Potassium Periodate

Dodecylbenzene (4.96 g. 20.4 mmol), potassium periodate ($KIO_4$, 2.74 g, 11.9 mmol), acetic anhydride (5.22 g) and acetic acid (10.10 g) were charged into a reactor, and stirred at 20-30° C. Separately, acetic acid (2.33 g) was charged into another reactor, and while cooling, concentrated sulfuric acid (2.95 g) was slowly added. While flowing nitrogen through the above reactor, the concentrated sulfuric acid-acetic acid mixture was added dropwise over 1 hour with stirring such that the reaction mixture temperature did not exceed 50° C. After the completion of addition, the temperature of the reaction mixture was raised to 50° C., and was further stirred for 7.2 hours.

Next, cyclohexane (10.08 g) was added to the reaction mixture, and the mixture was cooled to a temperature of 10° C. Further, water (9.98 g) was added, the temperature of the mixture was raised to 40° C., stirred for 0.5 hour, and by separating the phases, a cyclohexane solution (19.80 g) was obtained. On analysis of this solution by HPLC, the yield of the diaryliodonium compound was 81% on the basis of dodecylbenzene, the yield of the byproduct p-iodododecylbenzene was 3%, and the conversion of dodecylbenzene was 99.6%.

Example 5

Production of Diaryliodonium Compound Using Sodium Periodate

Dodecylbenzene (4.92 g, 20 mmol), sodium periodate ($NaIO_4$, 2.16 g, 10.1 mmol), acetic anhydride (4.04 g) and acetic acid (4.04 g) were charged into a reactor, and stirred at 20-30° C. Separately, acetic acid (2.00 g) was charged into another reactor, and while cooling, concentrated sulfuric acid (2.94 g) was slowly added. While flowing nitrogen through the above reactor, the concentrated sulfuric acid-acetic acid mixture was added dropwise over 1 hour with stirring such that the reaction mixture temperature did not exceed 50° C. After the completion of addition, the temperature of the reaction mixture was raised to 50° C., and was further stirred for 5.0 hours.

Next, cyclohexane (5.00 g) was added to the reaction mixture, and the mixture was cooled to a temperature of 10° C.

Further, water (5.02 g) was added, the temperature of the mixture was raised to 40° C., stirred for 0.5 hour, and by separating the phases, a cyclohexane solution (15.14 g) was obtained. On analysis of this solution by HPLC, the yield of the diaryliodonium compound was 87% on the basis of dodecylbenzene, the yield of the byproduct p-iodododecylbenzene was 0.6%, and the conversion of dodecylbenzene was 99.6%.

Example 6

Production of Diaryliodonium Compound Using Sodium Periodate

Dodecylbenzene (4.88 g, 19.8 mmol), sodium periodate ($NaIO_4$, 2.15 g, 10.1 mmol) and acetic anhydride (4.09 g) were charged into a reactor and stirred at 20-30° C. While flowing nitrogen through the above reactor, concentrated sulfuric acid (2.92 g) was added dropwise over 1 hour with stirring such that the reaction temperature did not exceed 50° C. After the completion of addition, the temperature of the reaction mixture was raised to 50° C., and stirred for additional 5 hours.

Next, ethylcyclohexane (7.02 g) was added to the reaction mixture, and the mixture was cooled to a temperature of 10° C. Further, water (5.50 g) was added, the temperature of the mixture was raised to 40° C., stirred for 0.5 hour, and by separating the phases, an ethyl cyclohexane solution (15.04 g) was obtained. On analysis of this solution by HPLC, the yield of the diaryliodonium compound was 77% on the basis of dodecylbenzene, the yield of the byproduct p-iodododecylbenzene was 0.7%, and the conversion of dodecylbenzene was 98.3%.

Comparison Example 2

Production of Diaryliodonium Compound Using Potassium Iodate

Dodecylbenzene (4.90 g, 19.9 mmol), potassium iodate ($KIO_3$, 2.16 g, 10.1 mmol), acetic anhydride (5.00 g) and acetic acid (8.00 g) were charged into a reactor and stirred at 20-30° C. Separately, acetic acid (2.00 g) was charged into another reactor, and while cooling, concentrated sulfuric acid (2.90 g) was slowly added. While flowing nitrogen through the above reactor, the concentrated sulfuric acid-acetic acid mixture was added dropwise over 1 hour with stirring such that the reaction mixture temperature did not exceed 40° C. After the completion of addition, the temperature of the reaction mixture was raised to 40° C., and was further stirred for 7.2 hours.

Next, cyclohexane (5.00 g) was added to the reaction mixture, and the mixture was cooled to a temperature of 10° C. Further, water (5.00 g) was added, the temperature of the mixture was raised to 40° C., stirred for 0.5 hour, and by separating the phases, a cyclohexane solution (15.00 g) was obtained. On analysis of this solution by HPLC, the yield of the diaryliodonium compound was 62% on the basis of dodecylbenzene, the yield of the byproduct p-iodododecylbenzene was 9%, and the conversion of dodecylbenzene was 88.6%.

Comparison Example 3

Production of Diaryliodonium Compound Using Potassium Iodate

Dodecylbenzene (4.97 g, 20.2 mmol), potassium iodate ($KIO_3$, 2.14 g, 10.0 mmol), acetic anhydride (4.08 g) and acetic acid (4.00 g) were charged into a reactor and stirred at 20-30° C. Separately, acetic acid (2.02 g) was charged into another reactor, and while cooling, concentrated sulfuric acid (2.94 g) was slowly added. While flowing nitrogen through the above reactor, the concentrated sulfuric acid-acetic acid mixture was added dropwise over 1 hour with stirring such that the reaction mixture temperature did not exceed 50° C. After the completion of addition, the temperature of the reaction mixture was raised to 50° C., and stirred for additional 5 hours.

Next, ethyl cyclohexane (7.04 g) was added to the reaction mixture, and the mixture was cooled to a temperature of 10° C. Further, water (5.08 g) was added, the temperature of the mixture was raised to 40° C., stirred for 0.5 hour, and by separating the phases, a ethyl cyclohexane solution (16.28 g) was obtained. On analysis of this solution by HPLC, the yield of the diaryliodonium compound was 61% on the basis of dodecylbenzene, the yield of the byproduct p-iodododecylbenzene was 12%, and the conversion of dodecylbenzene was 86.6%.

Comparison Example 4

Production of Diaryliodonium Compound without Using Acetic Anhydride

Dodecylbenzene (4.94 g, 20.0 mmol), sodium periodate ($NaIO_4$, 2.16 g, 10.1 mmol) and acetic acid (4.02 g) were charged into a reactor and stirred at 20-30° C. Separately, acetic acid (2.02 g) was charged into another reactor, and while cooling, concentrated sulfuric acid (2.94 g) was slowly added. While flowing nitrogen through the above reactor, the concentrated sulfuric acid-acetic acid mixture was added dropwise over 1 hour with stirring such that the reaction mixture temperature did not exceed 50° C. After the completion of addition, the temperature of the reaction mixture was raised to 50° C., and stirred for additional 5 hours.

Next, cyclohexane (7.00 g) was added to the reaction mixture, and the mixture was cooled to a temperature of 10° C. Further, water (5.14 g) was added, the temperature of the mixture was raised to 40° C., stirred for 0.5 hour, and by separating the phases, a cyclohexane solution (15.00 g) was obtained. On analysis of this solution by HPLC, the yield of the diaryliodonium compound was 37% on the basis of dodecylbenzene, the yield of the byproduct p-iodododecylbenzene was 0.8%, and the conversion of dodecylbenzene was 55.6%.

The above results are summarized in Table 3. Moreover, in Table 3, 'Conversion' is the extent of reaction of the starting compound dodecylbenzene, and is the value obtained by deducting the amount (%) of dodecylbenzene in the reaction mixture from 100%.

TABLE 3

| | I source | Acetic anhydride | Yield | Byproduct | Conversion |
|---|---|---|---|---|---|
| Example 4 | $KIO_4$ | Yes | 81% | 3% | 99.6% |
| Example 5 | $NaIO_4$ | Yes | 87% | 0.6% | 99.6% |
| Example 6 | $NaIO_4$ | Yes | 77% | 0.7% | 98.3% |
| Comparison example 2 | $KIO_3$ | Yes | 62% | 9% | 88.6% |
| Comparison example 3 | $KIO_3$ | Yes | 61% | 12% | 86.6% |
| Comparison example 4 | $NaIO_4$ | No | 37% | 0.8% | 55.6% |

As per the above results, the yields are lower when potassium iodate ($KIO_3$) is used (Comparison examples 2-3). As the residual amount of raw material dodecylbenzene is large due to low conversion, this may be thought to be the reason for the reaction not progressing satisfactorily. In addition, the amount of byproduct p-iodododecylbenzene formed is large. Since the separation of the p-iodododecylbenzene from the target diaryliodonium compound is difficult, large amounts of the byproduct significantly adversely affect subsequent processes.

Further, in spite of using sodium periodate (NaIO$_4$), the yields are extremely low when acetic anhydride is not used (Comparison example 4) although the amount of byproduct formed is also low. From these results, it is found that acetic anhydride plays an important role in the reaction for the production of diaryliodonium compounds from aryl compounds substituted with long chain alkyl groups.

In contrast to the Comparison examples above, according to the examples of the present invention of using potassium or sodium periodate in presence of acetic anhydride and concentrated sulfuric acid (Examples 4-6), the diaryliodonium compounds can be manufactured in excellent yields. In addition, as the amount of the byproduct p-iodododecylbenzene formed is also extremely low, high quality diaryliodonium compounds are obtained. Therefore, the method according to the present invention was proved to be an extremely superior method of production of diaryliodonium compounds.

Example 7

Production of Diaryliodonium Compound Using Sodium Periodate

Into a 4-neck flask equipped with a reflux condenser, dropping funnel, nitrogen inlet tube and a temperature are charged Alkene L (product of Nippon Oil Corporation, a mixture of benzene compounds substituted with alkyl groups of 10 to 13 carbon atoms, molecular weight: 241, 4.93 g), sodium periodate (NaIO$_4$, 2.14 g), acetic anhydride (4.09 g) and acetic acid (4.01 g) were added, and the atmosphere inside the reaction vessel was purged with nitrogen. A mixture of concentrated sulfuric acid (2.94 g) and acetic acid (2.00 g) was charged into the dropping funnel; and added dropwise over 1 hour such that the temperature of the reaction mixture did not exceed 40° C. After the completion of addition, the reaction mixture was stirred for 5 hours at 50° C. Then, while cooling, water (5.01 g) was added dropwise to the reaction mixture. Further, cyclohexane (5.00 g) was added to the reaction mixture and stirred for 30 minutes. From the reaction mixture that had separated into two layers, an organic phase (15.76 g) was obtained. Separately, a sodium iodide solution obtained by dissolving sodium iodide (1.50 g) in water (2.98 g) was added to the organic phase, and stirred for 30 minutes. The liquid layers of the reaction mixture were separated, and on addition of methanol (50.34 g) to the obtained organic phase, crystals were precipitated. The obtained crystals were separated from the solution by pressure filtration using a pressure filter of internal diameter 47 mm and applying a pressure of 0.14 MPaG. The filtration time at that time was 9.5 sec, and the obtained quantity of the filtrate was 55.4 g, and the rate of filtration was 12166 kg/h·m$^2$. By washing the obtained crystals with methanol (10.34 g) and drying under a reduced pressure at 60° C., crystals of diaryliodonium compound was obtained (weight: 4.50 g, yield: 60.4%).

On analysis of part of the obtained crystals with $^1$H-NMR, presence of the byproduct p-iodododecylbenzene was not detected.

Comparison Example 5

Production of Diaryliodonium Compound Using Potassium Iodate

Into a 4-neck flask equipped with a reflux condenser, dropping funnel, nitrogen inlet tube and thermometer were charged Alkene L (product of Nippon Oil Corporation, 5.01 g), potassium iodate (KIO$_3$, 2.16 g), acetic anhydride (5.23 g) and acetic acid (10.17 g) were added, and the atmosphere inside the reaction vessel was purged with nitrogen. A mixture of concentrated sulfuric acid (3.00 g) and acetic acid (2.03 g) was charged into the dropping funnel, and added dropwise over 1 hour such that the temperature of the reaction mixture did not exceed 40° C. After the completion of addition, the reaction mixture was stirred for 2 hours at 40° C. Then, while cooling, water (9.17 g) was added dropwise to the reaction mixture. Further, cyclohexane (4.55 g) was added to the reaction mixture and stirred for 30 minutes. From the reaction mixture that had separated into two layers, an organic phase 13.56 g) was obtained. Separately, a sodium iodide solution obtained by dissolving sodium iodide (3.06 g) in water (5.04 g) was added to the organic phase, and stirred for 30 minutes. The liquid layers of the reaction mixture were separated, and on addition of methanol (25.22 g) and ethanol (25.26 g), crystals were precipitated. The obtained crystals were separated from the solution by pressure filtration using a pressure filter of internal diameter 47 mm and applying a pressure of 0.14 MPaG. The filtration time at that time was 22 sec, and the obtained quantity of the filtrate was 54.4 g, and the rate of filtration was 5135 kg/h·m$^2$. By washing the obtained crystals with a mixture of methanol (3.84 g) and ethanol (3.12 g), and drying under reduced pressure at 60° C., crystals of diaryliodonium compound were obtained (weight: 3.24 g, yield: 42.9%).

On analysis of part of the obtained crystals with $^1$H-NMR, the byproduct p-iodododecylbenzene was found to be contained in an amount of 1.65 wt %.

As described above, when the diaryliodonium compound was prepared using potassium iodate, in spite of purification by crystallization, it is not possible to eliminate the byproduct p-iodo dodecylbenzene. If such a catalyst contained with p-iodododecylbenzene is used as a polymerization initiator, there is the problem of activity being low. Also, when the resulting crystals formed by crystallization are separated by filtration, the filtration rate is slow and it takes time, probably because the crystallization of target compound is poor due to the contamination with impurities.

In contrast, according to the method of the present invention using periodate, not only it is possible to produce the diaryliodonium compounds efficiently and in good yields, the incorporation of the byproduct of p-iodododecylbenzene can also be remarkably reduced.

In addition, when purifying by crystallization, it is possible to enhance the filtrate rate and reduce the time probably because of low amount of impurity and high crystallizability of the target compound. Such benefits, particularly in an industrial mass production of diaryliodonium compounds, will contribute to a significant improvement in production efficiency.

What is claimed is:

1. A diaryliodonium salt mixture, comprising 15 or more diaryliodonium salts represented by formula (I):

wherein $R^1$ and $R^2$ are independently $C_{8-20}$ alkyl groups, wherein a proportion of the most major diaryliodonium salt (I) is 30 mass % or less.

2. A process for production of a diaryliodonium salt mixture,
wherein the diaryliodonium salt mixture contains 15 or more diaryliodonium salts represented by formula (I):

wherein $R^1$ and $R^2$ independently represent $C_{8-20}$ alkyl groups, wherein a proportion of the most major diaryliodonium salt (I) is 30 mass % or less,
comprising the steps of:
synthesizing a diaryliodonium mixture containing 15 or more diaryliodonium compounds represented by formula (III) from an alkylaryl mixture containing 5 or more alkylaryl compounds represented by formula (II):

wherein $R^3$ is $C_{8-20}$ alkyl group; $R^1$ and $R^2$ are same as described earlier; and
adding a bromide salt or a iodide salt of an alkali metal or an alkaline earth metal to a solution of the mixture of diaryliodonium compounds (III).

3. The process according to claim 2, wherein a proportion of the most major alkylaryl compound (II) is 50 mass % or less in the alkylaryl mixture as a raw material.

4. The process according to claim 2, wherein a proportion of the most major diaryliodonium compound (III) is 50 mass % or less in the diaryliodonium mixture.

5. The process according to claim 2, wherein the number of the alkylaryl compound (II) contained in the alkylaryl mixture is 50 or less.

6. The process according to claim 2, wherein the iodide salt of an alkali metal or an alkaline earth metal is used in the adding step.

* * * * *